United States Patent [19]

Robertson, Jr. et al.

[11] Patent Number: 4,833,332
[45] Date of Patent: May 23, 1989

[54] SCANNING FLUORESCENT DETECTION SYSTEM

[75] Inventors: Charles W. Robertson, Jr., Rockland, Del.; Rudy J. Dam, Landenberg, Pa.; James M. Prober, Wilmington, Del.

[73] Assignee: E. I. Du Pont de Nemours and Company, Wilmington, Del.

[21] Appl. No.: 60,874

[22] Filed: Jun. 12, 1987

[51] Int. Cl.[4] .......................................... G01N 21/64
[52] U.S. Cl. .............................. 250/458.1; 250/461.2; 356/318; 356/417
[58] Field of Search ............... 250/461.1, 461.2, 458.1; 356/417, 318

[56] References Cited

U.S. PATENT DOCUMENTS

| | | | |
|---|---|---|---|
| 3,588,257 | 6/1971 | Folsom et al. | 356/417 |
| 3,764,512 | 10/1973 | Greenwood et al. | 204/299 |
| 4,152,723 | 5/1979 | McMahon et al. | 250/458.1 |
| 4,162,405 | 7/1979 | Chance et al. | 250/461 |
| 4,421,860 | 12/1983 | Elings et al. | 250/458.1 |
| 4,451,149 | 5/1984 | Noeller | 250/458.1 |
| 4,580,059 | 4/1986 | Wolfbeis et al. | 250/458.1 |
| 4,651,011 | 3/1987 | Ors et al. | 250/458.1 |
| 4,729,947 | 3/1988 | Middendorf et al. | 250/461.2 |

FOREIGN PATENT DOCUMENTS 3446635 6/1985 Fed. Rep. of Germany .

OTHER PUBLICATIONS

Merck Index, 9th Edition, Martha Windholz, editor, published by Merck & Co., Inc., Rahway, N.J., 1976, p. 1253.
"Fiber Optic Face Plate", Technical Brochure from the Incom, Inc. of Southbridge, Mass.
A. M. Maxam et al., Meth. in Enzyme, 65, 449–599, (1980).
F. Sanger et al., Proc. Nat. Acad. Sci., U.S.A., 74, 5463–5467, (1977).
L. M. Smith et al., Nature, 321: 674–679, (1986).
L. M. Smith et al., Nucleic Acids Research, 13, 2399–2412, (1985).

Primary Examiner—Janice A. Howell
Assistant Examiner—William F. Rauchholz

[57] ABSTRACT

A system for detecting the radiant energy emitted from different closely spaced species includes two detectors each having a large entrance angle for receiving the radiant energy, and wavelength selective filters between the detector and species, the transmission vs. wavelength characteristics being complementary, and means for ratioing functions of the detector outputs, the ratio being indicative of the identity of the species.

26 Claims, 7 Drawing Sheets

SCANNING FLUORESCENT DETECTION SYSTEM

CROSS REFERENCE TO RELATED APPLICATION

This application is related to an application entitled Method, System and Reagents for DNA Sequencing filed June 12, 1987, Ser. No. 07/057,566 by Prober et al.

FIELD OF THE INVENTION

This invention relates to a scanning fluorescent detection system and, more particularly, to apparatus suitable for use with a fluorescence-based DNA sequencer. This system is capable of distinguishing among similar fluorophores with relatively low levels of emission. A unique arrangement of a filter and fiber optic faceplate enables the system to monitor signals from relatively large detection areas containing multiple sample regions while still retaining the required optical characteristics of the combined filters.

BACKGROUND OF THE INVENTION

DNA sequencing, i.e., determining the sequence or order of the nucleotides or bases comprising the DNA, is one of the cornerstone analytical techniques of modern molecular biology. The development of reliable methods of sequencing has led to great advances in the understanding of the organization of genetic information and has made possible the manipulation of genetic material, i.e., genetic engineering.

These are currently two general methods for sequencing DNA: the Maxam-Gilbert chemical degradation method [A. M. Maxam et al., Meth. in Enzym. 65 499–599 (1980)] and the Sanger dideoxy chain termination method (F. Sanger, et al., Proc. Nat. Acad. Sci. USA 74 5463–5467 (1977)]. A common feature of these two techniques is the generation of four groups of labeled DNA fragments, each group having a family of labeled DNA fragments with each family containing fragments having differing numbers of nucleotides. The population of fragments within these groups all end with one of the four nucleotides or bases comprising the DNA. Both techniques also utilize a radioactive isotope, such as $^{32}P$ or $^{35}S$, as the means for labeling the fragments. The primary difference between the techniques is in the way the fragments are prepared.

In both methods, base sequence information which generally cannot be directly determined by physical methods must be converted into chain-length information which can be determined. This determination can be accomplished through electrophoretic separation. Under denaturing conditions (high temperature, urea present, etc.) short DNA fragments migrate through the electrophoresis medium as stiff rods. If a gel is employed for the electrophoresis, the DNA fragments will be sorted by size and result in a DNA sequence determination with single-base resolution up to several hundred bases.

The Sanger and Maxam-Gilbert methods for DNA sequencing are conceptually elegant and efficacious but they are operationally difficult, time-consuming, and often inaccurate. Many of the problems stem from the fact that the single radioisotopic reporter cannot distinguish between bases. The use of a single reporter to analyze the sequence of four bases lends considerable complexity to the overall process. To determine a full sequence, the four sets of fragments produced by either Maxam-Gilbert or Sanger methodology are subjected to electrophoresis in four parallel lanes. This results in the fragments being spacially resolved along the length of the gel according to their size. The pattern of labeled fragments is typically read by autoradiography which shows a continum of bands distributed between four lanes often referred to as a sequencing ladder. The ladder is read by visually observing the film and determining the lane in which the next band occurs for each step on the ladder. Thermally induced distortions in base mobility in the gel (this usually appears as a "smile effect" across the gel) can lead to difficulties in comparing the four lanes. These distortions often limit the number of bases that can be read on a single gel.

Problems relating to use of a single radioisotopic reporter revolve around its lack of sensitivity and the time required to evaluate a sample. The long times required for autoradiographic imaging aling with the necessity of using four parallel lanes force one into a "snapshot" mode of visualization. Since one needs simultaneous spatial resolution of a large number of bands one is forced to use large gels. This results in additional problems. Large gels are difficult to handle and are slow to run, adding even more time to the overall process.

Once the exposed image of the gel pattern is obtained, there is a problem of visual interpretation. Conversion of a sequencing ladder into a base sequence is a time-intensive, error prone process requiring the full attention of a highly skilled operator. Some mechanical aids do exist but the process of interpreting a sequence gel is still painstaking and slow. Finally, the use of radioactive materials has health risks associated with continued exposure over extended periods. Appropriate use of shielding and disposal procedures imposes some control of exposure levels, but elimination of isotope use would be highly desirable.

To solve these problems, efforts are underway to replace autoradiography with some alternate, non-radiosotopic reporter/detection system using fluorescence. DNA frequencies labeled with one or more fluorescent tags (fluorescent dyes) and excited with an appropriate light source give characteristic emissions from the tags which identify the fragments.

The use of a fluorescent tag as opposed to a radioisotopic level allows one to specify a DNA fragment detection system that responds to the optical parameters characterizing tag fluorescence. For example, the use of four different fluorescent tags, distinguishable on the basis of some emission characteristic (e.g., spectral distribution, life-time, polarization), allows one to uniquely link a given tag with the sequencing fragments associated with a given base. Once such a linkage is established, one can then combine and resolve the fragments from a single sample and make the base assignment directly on the basis of the chosen emission characteristic. When electrophoresis is chosen as a separation means, for example, a single sample containing DNA fragments with base-specific fluorescent tags can be separated in a single gel lane.

The "real-time" nature of fluorescence detection allows one either to scan in the electrophoresis direction a gel containing spatially resolved bands (resolution in space) or to monitor at a single point on the gel and detect bands of separated fragments as they pass in sequence through the detection zone (resolution in time). Large gels are not necessarily required to discriminate between the fragments when time resolution is selected. Furthermore, a "real-time", single lane detection mode is very amenable to fully automated base assignment and data transfer.

A known "real time" fluoresence-based DNA sequencing system developed by the California Institute of Technology is disclosed in at least one published patent application and at least two journal articles: L. M. Smith, West German Pat. Appl. DE No. 3446635 A1 (1985); L. M. Smith et al., Nucleic Acids Research, 13 2399–2412 (1985) and L. M. Smith et al., Nature, 321: 674–679 (1986). This system employs four sets of DNA sequencing fragments, each labeled with one of four specified fluorescent dyes. Unfortunately, the fluorescence (emission) maxima are spread over a large wavelength range (approximately 100 nm) to facilitate discrimination among the four dyes, but, the absoption (excitation) maxima for the dyes are comparably spread. This makes it difficult to efficiently excite all four dyes with a single monochromatic source and adequately detect the resulting emissions.

It would be preferable to use dyes with closely spaced absorption (and corresponding emission) spectra, selected to enhance the excitation efficiency. But such closely spaced spectra cause other difficulties. Recalls that a real time detection system for DNA sequencing must be able to distinguish between four different dye emission spectra in order to identify the individual labeled fragments. The emissions are typically of relatively low intensity. The detection system must have a high degree of selectivity and sensitivity (better than $10^{-16}$ moles DNA per band), and a means to minimize stray light and background noise, in order to meet desired performance characteristics. The system must also be able to monitor the detection area frequently enough to avoid missing any fragments that may migrate past the detection window between scans.

In order to effectively utilize an electrophoresis gel, a typical DNA sequencing experiment involves running multiple samples simultaneously in parallel lanes of a slab gel. Therefore, an excitation/detection system must also be able to monitor each lane of such a gel at essentially the same time. A system must be capable of monitoring a detection zone which spans the majority of the usable gel width. Typical sequencing gels have lanes that are 4–5 mm wide with 1–2 mm spacing between lanes. Therefore, in order to monitor a 10 lane gel, a detection system must excite and detect emissions from a region typically as wide as 70 mm.

Another fluorescence detection system developed for similar applications, is disclosed in a U.S. patent application Ser. No. 07/057,566 filed June 12, 1987 by Prober et al. This application discloses a system for detecting the presence of fluorescent energy from different species, typically dye-labeled DNA, following separation in time and/or space, and identifying the species. A set of four labels are chosen such that all four are efficently excited by a single source, yet have emission spectra that are similar but distinguishable in wavelength. Since differential perturbations in electrophoretic mobility of the attached DNA fragments are small, any disturbance to this behavior is minimized by using four tags that have similar molecular weights, shape and charge.

The scheme of Prober et al. provides for modulating and ratioing the signals corresponding to the fluorescent energies in two different wavelength ranges to obtain a resultant signal that determines the identity of the species. A dichoroic filter, with a transmission/reflection characteristic that various as a function of wavelength, or two filters with passbands that vary as a function of wavelength, effect the modulation. Two detectors are positioned respectively to receive the transmitted and reflected emissions and generate first and second signals that vary in different senses corresponding to the intensities of each. Preferably the dichroic filter characteristic has a relatively sharp transition from transmission to reflection which occurs near the center of the species emission spectra.

This system overcomes many of the problems of Smith et al. and has the ability to distinguish in real time between relatively small wavelength differences in emission spectra, while maintaining a relatively high degree of sensitivity. Further, the system delivers a high portion of the usable light onto the two photometric detectors to maintain continuous monitoring of the gel containing the fluorescent species.

Both of the systems described above operate a fixed light beam and fixed detectors which together can monitor only a single point within the monitoring region. In order to monitor more than one spacial position (lane or lane position) of a gel, either the light beam must be scanned while providing a means to detect the emissions from the dyes, or the gel must by physically shifted while holding the beam fixed. The latter of the two alternatives, moving the gel, is not always practical since a large electrophoresis gel along with its associated buffer reservoirs are physically cumbersome. The other alternative, moving the beam while the gel is stationary, has its own problems since the detectors must remain closely coupled to sources of emission to prevent the entry of stray light and maximize collection of the emitted light.

One method of accomplishing this task is to physically move either of the two previously discussed detection systems and their associated optics and light beam so that several lanes in the gel are effectively scanned. This type of system has the disadvantage of being mechanically complex while introducing additional noise into the system. Reliability and the high costs associated with this type of system would also be a concern.

Another known "scanning" detection system is discussed in U.S. Pat. No. 3,764,512 issued to Green et al. This system discloses a laser scanning electrophoresis instrument and system for determining the electrokinetic or zeta potential of dispersed particles in an aqueous solution. This system utilizes a galvanometer mirror to scan a laser light beam across an electrophoresis medium. The system is not capable of detecting multiple samples moving perpendicular to the scanning motion of the beam.

Another scanning system is disclosed in U.S. Pat. No. 4,162,405, Chance et al. which describes an apparatus for measuring the heterogeneity of oxygen delivery to perfused and in situ organs. A laser is employed as a flying spot scanning excitation source and uses two photodetectors to monitor the emission signal and excitation wavelength light. Although an x-y scanner is used to move the laser beam over the sample area, the total scanned area is only 1 cm by 1 cm. (As mentioned earlier for a multiple sample DNA sequencer, a sample area 7 times wider is needed).

To implement the schemes of Chance et al. for a large area, the detectors must be either larger in size, or located further from the sample thus diminishing the collection efficiency. Furthermore, the detection of closely spaced emission spectra of relatively low light intensities in the presence of a much more intense excitation source requires the selective transmission properties offered by interference filters. In order to monitor a relatively large spacial area, both large detectors and large filters must be used. Unfortunately, large interference filters that collect light even a large solid angle are subject to transmission properties which vary with the angle of incidence of the light. Thus, when placed close to the emission source, light impinging on the filter with an angle of incidence greater than about 22 degrees can experience significantly less rejection of the excitation light than light at normal incidence. Consequently, if the filter subtends a relatively large solid angle with respect to the source of emission, the overall excitation wavelength rejection properties of the filter will be compromised due to leakage of excitation light entering at the higher angles of incidence.

SUMMARY OF THE INVENTION

Many of the above noted problems of the prior art radiant energy detecting systems are overcome by this invention which has particular application to a DNA sequencing system. This invention finds use in a system for detecting the presence of radiant energy from different species, typically dye-labeled DNA, following separation in time and/or space, and identifying the species, the system having first detection means responsive to the radiant energy emitted by the species of generating a first signal that varies in amplitude in a first sense as a function of the nature of the species, second detection means responsive to the radiant energy for generating a second signal that varies in amplitude in a second sense different than the first sense as a function of the nature of the species, and third means responsive to the first and second signals for obtaining a third signal corresponding to the ratio of functions of the first and second signals, the amplitude of the third signal being indicative of the identity of each of the species.

The invention is an improvement of such system wherein the first and second means each include: a detector having a large solid entrance angle positioned adjacent to the species to receive radiant energy emitted from the species, and a wavelength selective filter means positioned between each respective detector and the species, each wavelength filter means having transmission vs. wavelength characteristics that are complementary, and wherein one of the first and second detection means includes a transmission filter means for rejecting radiant energy incident on a detector at an angle greater than a predetermined value.

Preferably, the species are excited by a beam of radiant energy from a laser and the system includes means to separate molecules (typically fragments of DNA) labelled with emitting species of materials. The detection means are positioned on opposite sides of the region propagating the laser beam of energy in which beam is swept across the separation means to excite the species in sequence. The wavelength selective filters have a transition in their transmission vs. wavelength characteristics centered at about the middle of the species' radiant energy spectra. The transmission filter has an extra mural absorber among plural optical fibers positioned to have parallel generatrices transverse to the first and second detectors.

This system is optically efficient and does not require the use of lenses or other collection optics. It is capable of and does, by the use of detectors having a wide entrance angle, view large areas capable of accommodating plural electrophoresis lanes. These plural lanes are sequentially and repetitively scanned. Because of these efficiencies, the system can operate using low levels of emitted radiant energy. The only moving part required in the system is an optical element which effects the laser scanning. The use of the transmission filters and associated extra mural absorbers substantially reduce extraneous light impinging on the detector. The system is capable of detecting and distinguishing the radiant energy emitted from plural sources that emit energy at different but closely spaced wavelengths.

BRIEF DESCRIPTION OF THE DRAWINGS

The invention may be more fully understood from the following detailed description thereof taken in connection with accompanying drawings which form a part of this application and in which.

DETAILED DESCRIPTION OF THE PREFERRED EMBODIMENT

Figure 1:
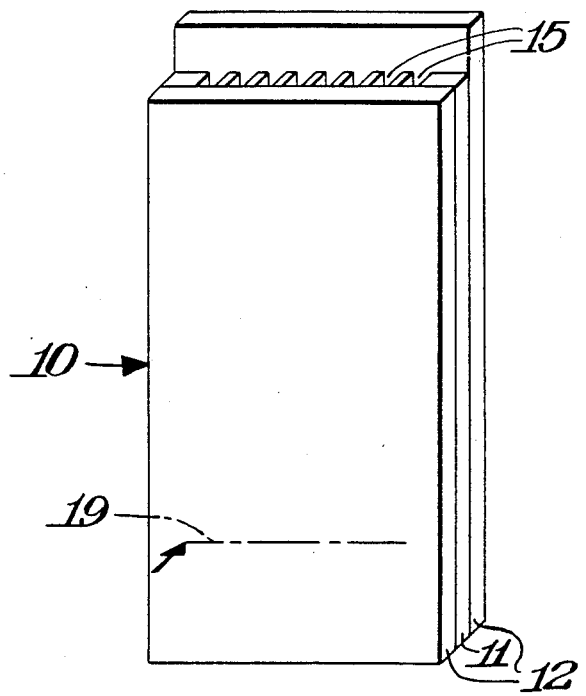
FIG. 1 is an isometric view of the electrophoresis gel slab showing plural sample wells and lanes.
Figure 2:
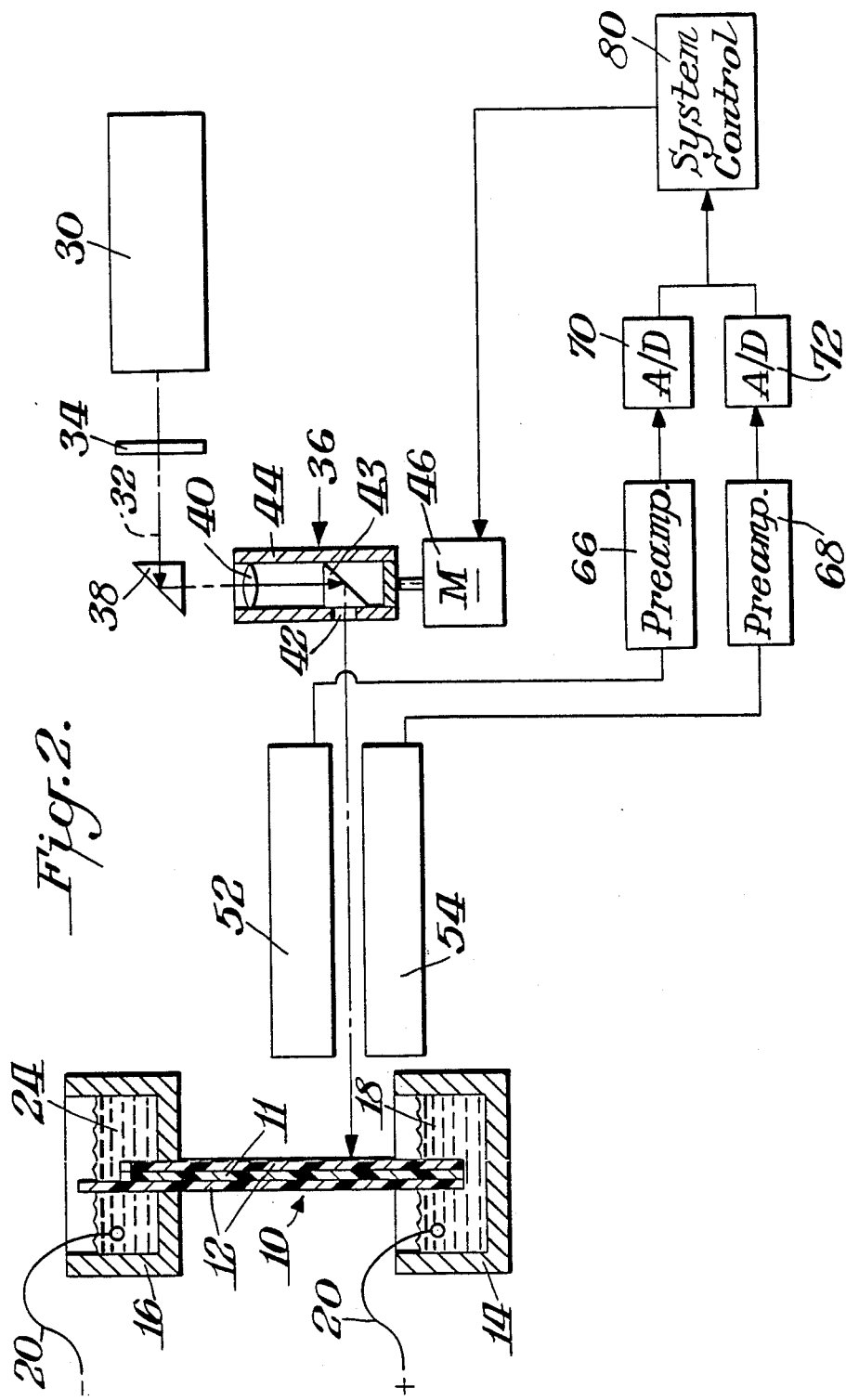
FIG. 2 is a partial diagrammatic layout of a system constructed in accordance with this invention for detecting the presence of radiant energy from different sources that each emit energy at different but closely spaced wavelengths.

The radiation from very closely spaced emission bands may be detected using the system of this invention. These closely spaced emissions are produced from preselected species which typically act as reporters and are irreversibly bound to materials that are to be analyzed. Acceptable reporters are generally one or more species chosen for their ability to emit radiation over a narrow range of wavelengths, typically between a 50 and 100 nm range, preferably over a 20 to 50 nm range. Preferably, the peak maxima should be spaced no closer than 2 nm. One reporter species may be capable of emitting energy at more than one wavelength, depending upon the manner of attachment to the materials of interest and the conditions of analysis in the system. However, individual reporters with unique emission characteristics in the system are more conventionally chosen to emit radiation in the wavelength range to be detected. Since the preferred form of the invention is directed to detecting reporter-labeled DNA sequencing fragments, it will be described in that context. It is to be understood, however, that the invention may be used to detect any light emitting labelled samples and is particularly advantageous where the emission radiation has closely spaced wavelengths. The invention may be used to detect, for example, fluorescense, chemiluminescence, and the like. Thus dye labelled DNA sequencing fragments are passed through an electrophoresis apparatus for separation. For this purpose, as is illustrated in FIGS. 1 and 2, the electrophoresis may be carried out by a suitable slab 10 arrangement typically having a thickness of about 0.3 mm and about 40 centimeters long and 15 centimeters wide. Other sizes may be used as appropriate. This slab 10 has a suitable gel 11, typically 6% polyacrylamide; sandwiched between glass or low fluorescing plastic supports 12.

The slab 10 is typically placed in an upright position in a holder with the upper end of the slab 10 extending through and into an upper container 16 holding a buffer 24 and downwardly into a second container 14 also holding a buffer 18. The buffer solution could be any suitable buffer such as that obtained from a solution consisting of 0.1M tris, 0.1M boric acid, and 0.05M $Na_2$ EDTA, with a final pH of approximately 8.3. In this manner, the buffer contacts the gel at either end of the slab in order to make electrical contact therewith.

With this arrangement, a sample containing reporter dye-labeled DNA fragments can be pipetted into cavities 15 that are created at the top of the gel 11 and define separation lanes. The reservoir containers 14 and 16 are filled with buffer solutions 18 and 24. An electrical circuit is then completed through the terminals 20 in reservoir containers 14 and 16. A suitable electrical field (typically 50 volts/cm) is needed to obtain separations for gels of this particular length and thickness. The positive electrode is located at the lower end of the slab 10 to cause the DNA fragments to migrate downwardly. Under these conditions, as the fragments migrate through the gel they are separated spatially into bands (not shown).

These bands are detected by the system and apparatus of this invention as they migrate downwardly in a detection zone 19 located near the bottom of the slab 10. In this zone 19, the DNA fragments are irradiated by a laser beam 32 of appropriate excitation wavelength and the different reporters attached to the several fragments emit detectable radiation. Since the reporters and their attachment to the DNA fragments are not the subject of this invention, such will not be described in detail. However, an example of appropriate reporters is described in the copending Prober et al patent application.

Four fluorescent dyes were selected with emission maxima at 505, 512, 519, and 526 nm. These maxima may tend to shift somewhat when in the environment of gel electrophoresis. These emission characteristics were created by the appropriate chemical group substitutions, such as methyl groups, at specified loci in the parent compound (9-carboxyethyl-6-hydroxy-3-oxo-3H-xanthene). Each of the four dyes prepared have reactive carboxy groups provided by a sarcosinyl moiety covalently bound to the 9-position of the parent compound, which are capable of forming covalent attachments with amine groups in linking moieties that join the dyes with selected nucleotides. Useful linking moieties found are a group of alkynylamine derivatives which contain a terminal amino group that can form covalent attachments with the dye carboxy groups. A preferred linker is a 3-aminopropynyl derivative which is covalently attached to the 5-position of uracil (T) or cytosine (C), or to the 7-position of deazaguanine (d-G) or deazaadenine (d-A).

Appropriate linker-nucleotide derivatives for use in the system of this invention were prepared with 2',3'-deoxyribonucleotides, which are known to serve as DNA chain terminating substrates for DNA polymerases. It was found that covalent attachment of the aminopropynyl-2',3'-dideoxynucleotides to the fluorescent dyes in appropriate combinations, did not substantially diminish the chain terminating properties of the unsubstituted 2',3'-dideoxynucleotides. The four dye-linker-dideoxynucleotides A,G,C,T selected are illustrated by the structures:

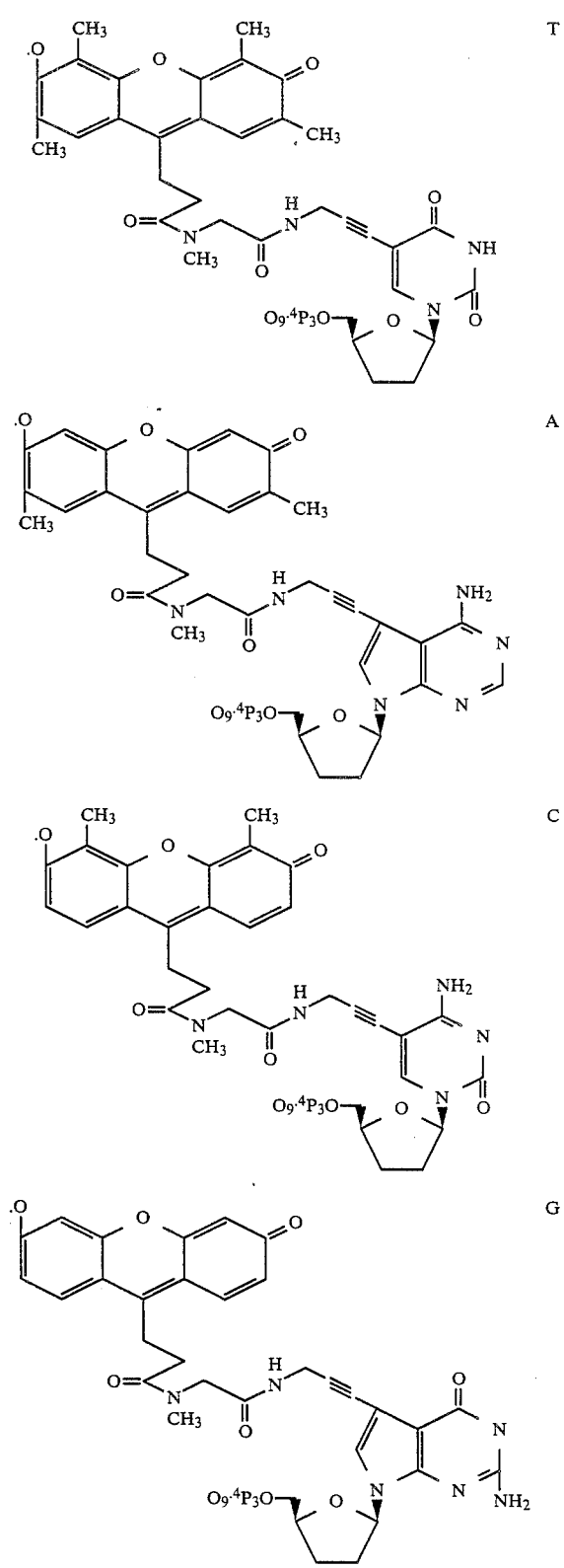

They were found to serve as useful chain terminating substrates for reverse transcriptase (avian myeloblastosis virus) in a modification of the well-known Sanger DNA sequencing method. The classical Sanger method uses a primer, DNA template, DNA polymerase I (Klenow fragment), three unlabelled deoxynucleotides and one radiolabeled deoxynucleotide in each of four reaction vessels that each contain one of four 2',3'-dideoxynucleotides, which correspond to the four DNA bases (A,C,T,G).

Appropriate reaction conditions are created which allow the polymerase to copy the template by adding nucleotides to the 3' end of the primer. A multitude of reactions occur simultaneously on many primer copies to produce DNA fragments of varying length which all contain the radiolabel at appropriate nucleotides in each fragment, and which also irreversibly terminate in one of the four dideoynucleotides. This set of fragments is typically separated on a polyacrylamide slab electrophoresis gel in four lanes, one lane corresponding to each of the four dideoxynucleotide reaction mixtures. After the fragments have been separated, a photographic film is placed on the gel, exposed under approprate conditions, and a DNA sequence is inferred from reading the pattern of bands created by the radiolabel on the film in order of their appearance in the four lanes from the bottom of the gel.

The modifications permitted by using these dye-labelled terminators include omitting the radiolabeled nucleotide and substituting the dye-labelled chain terminators for the unlabeled 2',3'-dideoxynucleotides. Reaction mixtures (actually a single reaction member can be used) will now contain fragments which are labeled on their 3' ends with a fluorophore that corresponds to each of four DNA bases. The reaction mixture(s) are combined and electrophoretically separated. Sequence is inferred by the order of appearance of bands being resolved in time or space that are revealed by the presence of fluorescent radiation. Therefore, the fluorescent dye-labelled dideoxynucleotides previously described are the preferred sources of closely spaced emitted radiation to be detected in the system and method of this invention. An alternative source of emitted radiation which can also be useful in the system and method of this invention are the fluorophores described in the Smith et al. application. Their use would require selection of the appropriate laser frequencies and wavelengths of the preselected filters.

The optical arrangement for irradiating the lanes of the electrophoresis slab 10 is shown in FIG. 2. The system and apparatus of FIG. 2 may be used with any fluorescent or other type system to distinguish between and measure the intensity of closely spaced emission radiation bands. However, it will be described by way of example of detecting the emissions from DNA fragments labeled with the particular reporters (dyes) set forth in the Prober et al. application, which application is incorporated herein by reference. The dyes described in Prober et al. have peak emission wavelengths of about 505, 512, 519, and 526 nm. It includes a laser 30 which is selected to provide an exciting beam of radiation 32, with a specific wavelength determined as a function of the excitation wavelengths of the fluorophores used. The specific source used with the dye fluorophores disclosed in Prober et al. is an argon ion laser with a wavelength of 488 nm and a 0.8 mm diameter light beam 32 operated at about 50 mW. The light beam 32 passes through an excitation filter 34 and is then directed into scanning optics 36. The filter 34 is selected block out any undesired excitation wavelengths that could otherwise interfere with the detection process. However, for sufficiently spectrally pure lasers this filter may be omitted.

The scanning optics 36 include a prism or mirror 38 mounted on a fixed support (not shown), an astigmatic focusing lens 40, a second prism or mirror 43, and a cylindrical optic support 44 all mounted to the shaft of a stepping motor 46. The beam 32, upon entering the scanning optics 36 is first directed downward by the prism 38 into the cylindrical opening of the optical support 44 and through the focusing lens 40. Prism 38 serves to direct the beam from the laser into the scanning optics 36 thus facilitating convenient placement of the laser 30. The light beam, passing through the focusing lens 40 is concentrated into an elliptical spot, in a preferred case of about 0.2 mm × 1—2 mm in cross-section. The focused light beam 32 is directed through an exit aperture 42 by the second prism 43. The optic support 44 is mounted to the shaft of the stepping motor 46 such that by actuating the stepping motor 46, the lens 40 and the prism 43 are rotated to cause the light beam 32 to angularly scan, in a horizontal plane perpendicular to the shaft axis and to the plane of the gel 11. This light beam 32 is directed at the detection zone 19 of the electrophoresis slab 10.

The light beam 32, upon entering the slab 10 excites the reporter material, here fluorescent dye labelled DNA fragments, as they migrate through the detection zone 19, causing them to fluoresce at wavelengths shifted from the excitation wavelength. The peak emission wavelengths for the dyes described in Prober et al. are about 505, 512, 519, and 526 nm; however the system is adaptable to discriminate wavelengths associated with other sets of dyes with closely spaced emission bands. Furthermore, while a laser source is preferred since it allows a minimum of extraneous filtering and optics, other sources including a non-coherent source such as a xenon arc lamp could be used.

Figure 3:
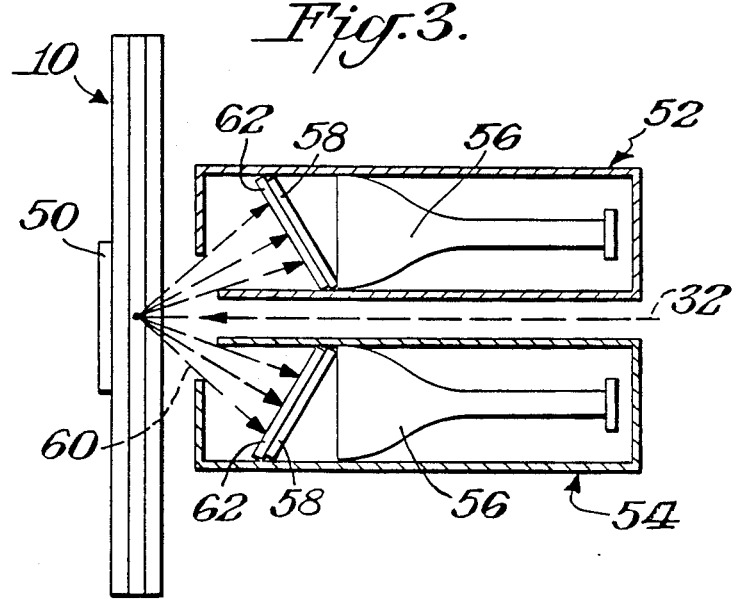
FIG. 3 is a side elevation view of the detector/filter arrangement for detecting the presence of radiant energy.

To increase the total radiant energy emitted by the fluorescent species, a reflective surface 50 (FIG. 3) can be positioned opposite from the excitation source. In the preferred apparatus, a mirrored surface is deposited directly onto the outside of the outer plate 12 which supports or contains the gel. The excitation light 32 which is not absorbed by the emitting species continues through the plate 12 and is reflected back towards the species by surface 50 to provide essentially twice the amount of excitation light. Additionally, the light given off by the fluorescent fragments is emitted in all directions so that light directed towards the reflective surface 50 is reflected also. The net increase in fluorescent signal available for detection is approximately 4 times the amount available without the reflective surface. The preferred method of providing a reflective surface is accomplished by coating the outside of the plate which supports the gel 10. Alternatively, a mirror could be external to the glass but the increased number of interfaces that the light passes through would cause additional undesirable scattered excitation light. The radiant energy or light emitted by the fluorescent species is collected by two suitably positioned upper and lower photodetector modules 52 and 54, respectively. These detector modules can be seen most clearly in FIG. 3 in which the details of their construction is shown.

Figure 4:
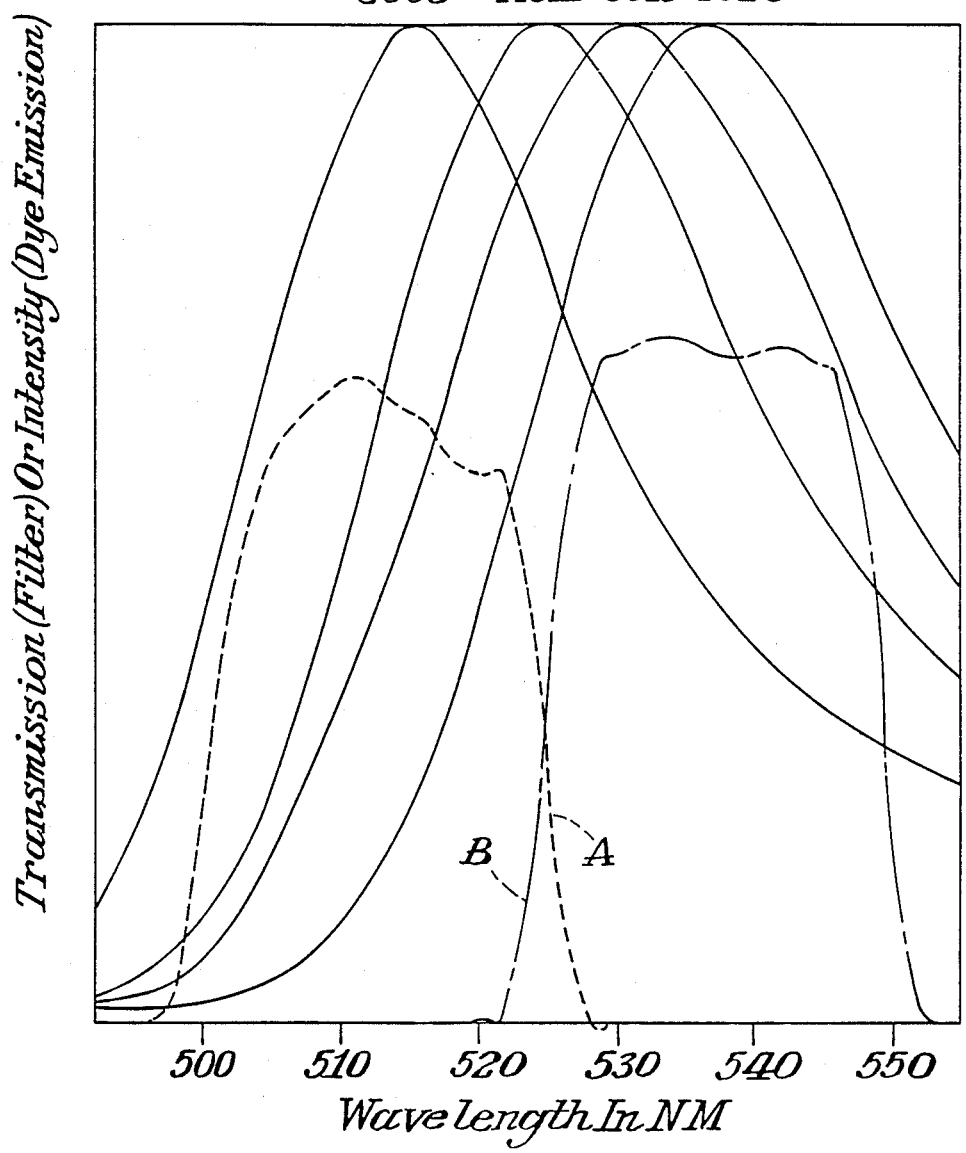
FIG. 4 is a graph depicting the complementary filter transmission characteristics as a function of wavelength.

In accordance with this invention, the modules 52 and 54 are positioned above and below the plane of scanning of the light beam. The modules are light tight in such a way as to eliminate stray light not directly coming from the excitation region. Each module comprises a photomultiplier tube (PMT) 56 of conventional type having a wide entrance area. A suitable photomultiplier tube is the Hamamatsu R1612. Each module 52, 54 also has a separate wavelength selective filter 58 positioned between its PMT 56 and the fluorescent species in the gel slab 10. The filters 58 preferably are custom interference filters which may be obtained from Barr Associates in Westford, MA, which have complementary transmission band characteristics as shown in FIG. 4 and are positioned to be transverse (preferably perpendicular on average) to the light 60 emitted from the species. This positioning permits them to operate to optimum efficiency as will be described. One filter 58 having a transmission characteristic denoted by the waveform A of FIG. 4 is seen to largely pass the lower emission wavelengths and reject the higher emission wavelengths. The other filter 58 having a transmission characteristic denoted by the waveform B (FIG. 4) does precisely the reverse—it largely passes the higher wavelengths and largely rejects the lower wavelengths.

Finally, each module 52, 54 has a transmission filter 62 positioned between the wavelength selective filter 58 for that module and the emitting species. These filters can be reversed. Each transmission filter 62 rejects incident light entering the filter at off axis angles greater than a predetermined angle. The two wavelength selective filters 58 enable the system to distinguish between closely spaced emission spectra. Light impinging on these wavelength filters 58 will either be transmitted, absorbed, or reflected. The emission spectra of the four illustrative dyes selected, namely G505, A512, C519, and T526, are illustrated in FIG. 4. The transmission filters 58 have been chosen to have complementary transmissive characteristics corresponding to curves A and B in FIG. 4 as described.

The two filters 58 are seen to have roughly complementary transmission vs. wavelength characteristics in the emission wavelength region of the four dyes, with the transition wavelengths occurring near the center or middle of the species radiant energy spectra. As the fluorescence spectrum shifts from the shorter to longer wavelengths, the ratio of light transmitted through the upper filter 58 (in the drawing) to light transmitted through lower filter 58 In the drawing) changes in a continuous manner. The most suitable filters for this application are interference filters which have both a high relative transmission and high blocking at the excitation wavelength. Although these particular filters have been chosen to accommodate the particular dyes selected from this application, a different set of dyes could be suitably differentiated with other filter sets based on these principles.

The detectors and corresponding filters are selected to have a relatively large area for this application. The detectors 56, preferably photomultiplier tubes, have large entrance windows nominally about 8 by 3.5 cm. In this way, a relatively large area 19 on the gel slab, can be monitored without the need for imaging optics which inherently create inefficiencies in the light collection and are sources of scattered light. The detectors 56 in this system are positioned approximately 2-3 cm. from the emitting species such that multiple samples can be continuously monitored with high light collection efficiency. Under these conditions, it may be said that the detectors have a large solid entrance angle.

As mentioned above this ordinarily would lead to the transmission of undesired high angle off normal (to the detectors) scattered excitation light. This occurs because at off-normal angles, the path length through the deposited layers (cavities) of the filters 58 is changed significantly, thereby shifting the filter characteristics toward the shorter wavelengths. (Changes in bandwidth and the peak transmission are minimal for small incident angles with respect to the normal to the filters.) Since the sample emits radiation from the detection zone in all directions the detection of some off-axis radiation is inevitable. Light impinging on the transmission filters 62 near the normal angle is desirable, but using large detectors spaced a fixed distance from the emitting species allows scattered excitation light as well as fluorescent emitted light to impinge over the entire surface of the filter at relatively oblique angles. This light is then transmitted through the filter independent of the specified filter characteristics.

In accordance with this invention, this problem is solved by the use of special transmission filters 62 coupled with the wavelength filters 58 such that the light impinging on the wavelength filters 58 is limited to a fixed range of angles close to the normal direction. The majority of the light which is impinging at an angle greater than a cut off value is either rejected or absorbed. If additional off-angled rejection is necessary, this invention can be combined with appropriate baffling, the use of colored filter glass or other known means.

A known device 62, useful for the transmission filters 62, having characteristics capable of rejecting off-angle light, is manufactured by INCOM located in Southbridge, Mass. This device consists of a tightly packed bundle of optic fibers fused together, each fiber having a diameter of approximately 10 microns. The bundle is cut transversely across the fibers to produce an optic element of a desired thickness. Since each one of the fibers in the element has a nominal numerical aperture of about 0.35 only light impinging within a $\pm 21°$ angle is allowed to be transmitted. Light impinging at angles greater than the acceptance angle is either rejected by first surface reflection or is passed through the cladding of the transmission fiber. Light which passes through the cladding can continue through the next adjacent fiber in the same manner to finally reach the opposite surface of the plate and exit at an angle similar to the original angle of incidence. This particular light will impinge on the wavelength filters 58 in each module 52, 54 at an undesirable angle and avoid the designed filter characteristics. To eliminate the occurrence of this type of light transmission through the fiber plate, 3-6% "extra mural absorber" (EMA) fibers are evenly dispersed throughout the bundle. The normal distribution of these fibers creates an absorbing barrier that dramatically attenuates light which passes through the walls of the optic fibers but does not affect the internally reflected light that propagates through each fiber in the plate.

Figure 5A:
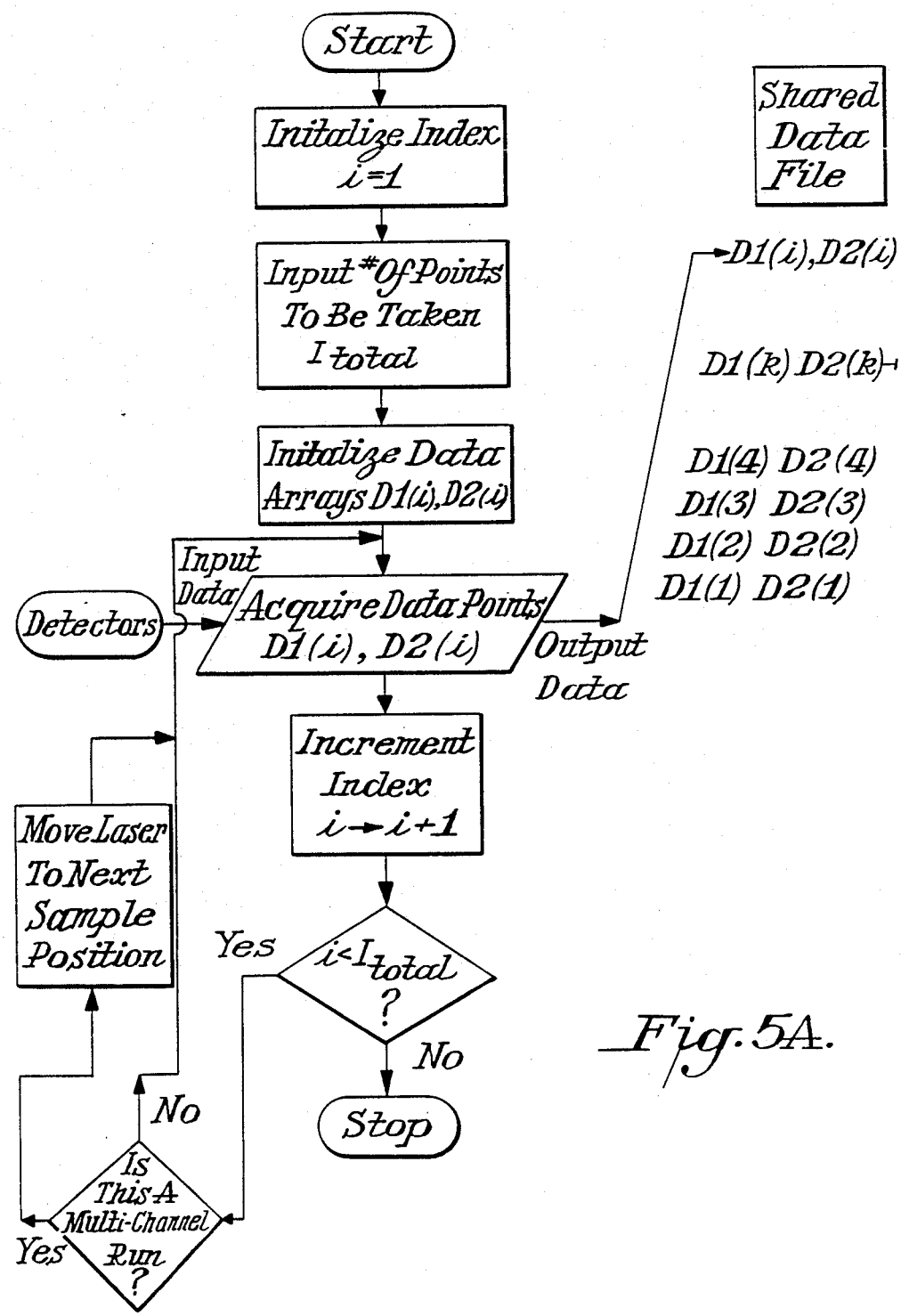
FIGS. 5A, 5B, and 5C are flow diagrams describing the routines and subroutines used to obtain sequence of DNA fragments using the systems of this invention.
Figure 5B:
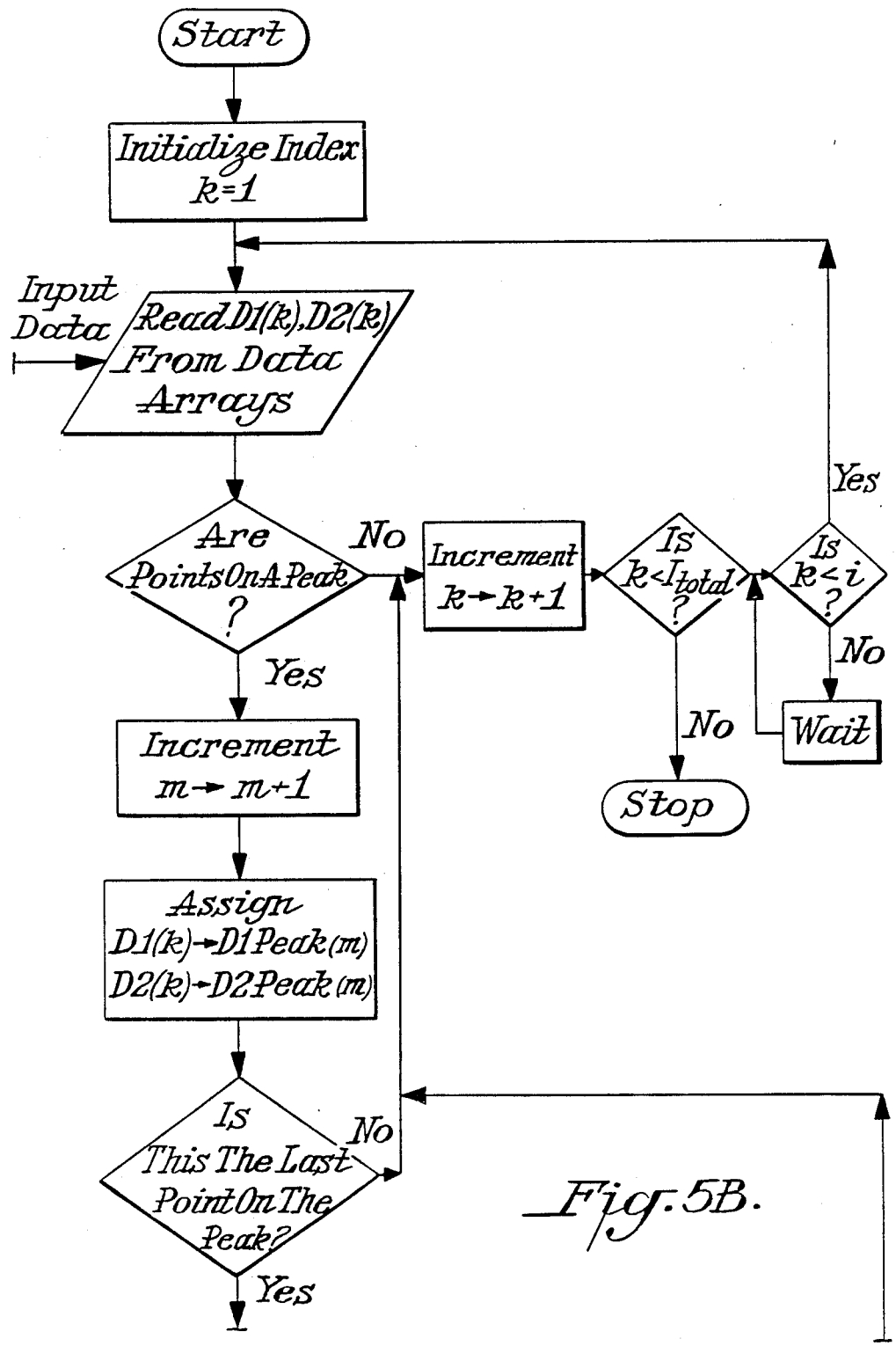
Figure 5C:
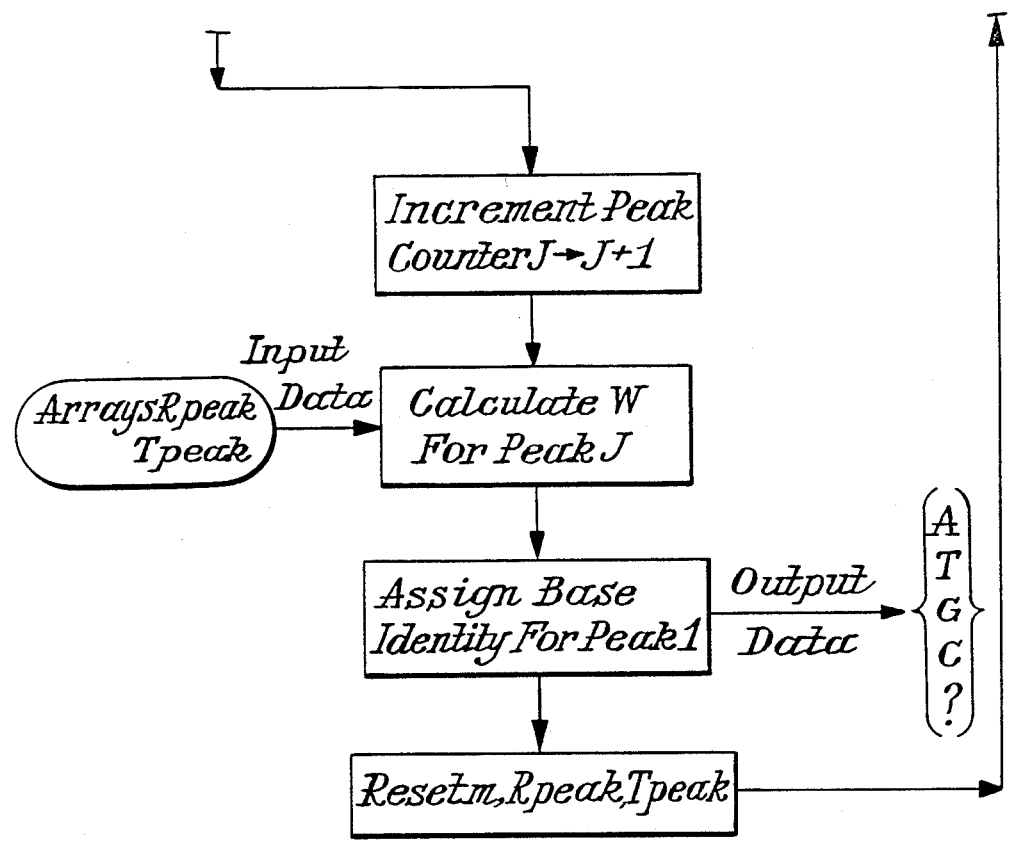

Returning to FIGS. 2 and 3, light transmitted through the respective filter systems 62-58 is directed to the respective detectors 56. The electrical signals from the detectors are then passed via respective preamplifiers 66, 68 and to respective analog to digital (A/D) converters 70, 72 and thence to a system controller 80. The task of the system controller 80 may be performed by a small computer such as an IBM PC. A function of the system controller 80, which is described by the flow diagram FIGS. 5A, 5B and 5C is to compute the ratio of the two signal functions (the emission intensities on the PMT's 56 for each different emission wavelength) among other control tasks. The wavelength filters 58 modulate the intensity of the signals in each of the different wavelength regions according to wavelength, i.e., from one detector, the shorter wavelength emissions will have a lower amplitude signal value and the longer wavelength emissions will have a higher amplitude. The reverse is true for the other detector since the filters have complementary characteristics as described.

Thus, as a particular species, i.e., a dye-labeled DNA fragment, following separation in space in the gel slab, passes through the detection zone 19 of gel slab 10, its emission spectra will generate two signals, one at the output of each detector 56, that vary in amplitude as a function of the emitted wavelength and time (because of the movement through gel slab 10). The amplitude modulated light signals are at this point converted to electrical signals which are then digitized for such processing as described. After conversion, the functions of the two digital signals are ratioed, i.e., to obtain the quotient of the first and second signals of fluorescent light for each fluorophore. The magnitude of the ratio signal is indicative of the identity of the species. Actually the ratio signals amplitudes for each dye tends to fall into distinct clusters or groupings which are readily distinguishable.

As used herein the term "closely spaced" in terms of the emission characteristics of the dyes or fluorophores is a somewhat relative term. The minimum spacing between the center of emission of the dyes is large enough such that the difference in ratios of signals from the two detectors for any two adjacent dyes is distinguishable above the inherent system noise.

In order to improve dye detection selectivity, the filter characteristics can be further optimized. This can be accomplished by choosing filters with characteristics that change substantially over the different dye emission spectra. However, to distinguish a closely spaced group of dyes, it is preferable to have relatively sharp filter transitions that occur near the center wavelength of the group of dye emissions in order to evenly distribute the change in ratio of signals in the two filters for the different emission spectra. The characteristics of an individual filter can also be fine-tuned to a degree by slightly varying the angle of incidence of the fiber optic faceplate output flux relative to the interference filter normal due to the idiosyncracies of interference filters as discussed previously.

In many cases, the extra mural adsorption of the transmission filter 62 need be used for the wavelength filter having a passband closest to the excitation wavelength of the laser needs to be more than the other transmission filter. In this example where the exciting laser operates at 488 $\mu$m, the wavelength filter 58 having the passband A (FIG. 4) requires a transmission filter 62 with twice the EMA as used with the wavelength filter 58 having the passband B (FIG. 4). In some cases only one transmission filter is needed.

SYSTEM CONTROL

The system controller 80 converts the digital signals received from the A/D converters 70 and 72 into DNA sequence information. In most cases, this will be done by a computer executing programs in real time. This means that data is processed and sequence information is determined concurrently with the acquisition of raw data from the detectors.

Conceptually, the operation of the system controller may be broken down into three interacting processes: data acquisition or input, data analysis, and output. The processes interact by sharing data and by sharing timing information which keeps them "in step" and prevents them from interfering with one another. The details of how these interactions are accomplished depend on the language and hardware chosen and is not of fundamental concern.

The data acquisition and processing so performed to obtain DNA base sequence information can be best understood by referring to the flow charts in FIGS. 5A, 5B, and 5C. These figures represent a general method by which the raw detector input from the scanning fluorescent detection system may be converted into output, i.e., the DNA sequence of the sample. In this discussion the following terms shall mean:

1. i is the index of the current data point being acquired. This point is acquired at time t(i) min.
2. k is the index of the current data point being processed taken at t(k)min. In a general data processing scheme, k need not equal i, i.e. data processing may lag behind data acquisition.
3. t(i) is an array of time points at which data was acquired. Example: t(5)=6.2 min would indicate the 5th data point was acquired at 6.2 minutes after the start of the run.
4. D1(i) is the array of data from the first detector.
5. D2(i) is the array of data from the second detector.
6. J is a count of peaks detected.
7. N is the number of data points across a given peak.
8. m is an index of points across a defined peak in either D1(i) of D2(i). m=1 at the start of a peak; m=n at the end of a peak.
9. W is a function (e.g. the ratio) of the detector outputs D1(i) and D2(i), the value of which determines the identity of the DNA base corresponding to a given peak.

DATA ACQUISITION

A general data acquisition process for a single channel is shown by the flow chart 5A. The index i, which points to the current acquired data, is initialized. The program accepts an input which determines how long the run will take, i.e. the total number of data points I$_{(total)}$. After the raw data arrays D1 and D2 are initialized, the process enters an acquisition loop. Data are read from the detectors, digitized, and placed in the arrays as D1(i) and D2(i) for detector 52 and detector 54, respectively, acquired at time t(i). (For the purposes of this discussion, the two readings are simultaneous.) At this point, the index i is incremented and compared to I$_{(total)}$. If i is less than I$_{(total)}$, the acquisition loop is repeated. If i equals I$_{(total)}$, the run is stopped. In a more elaborate scheme, the program could sense when to end the run automatically by measuring several performance parameters (such as signal/noise ratio, peak resolution, or uncertainty in assigning bases) at each peak of the run. If a combination of such factors failed to meet present criteria, the run would be terminated by the computer.

The primary data input is the raw data from the detectors and the output is stored in the data arrays D1(i) and D2(i) which are shared between the acquisition and the data analysis processes. This scheme is depicted schematically in FIG. 5B. Although the two programs run independently and simultaneously, some control information must be passed between them in order to maintain proper timing. For example, the processing steps cannot be allowed to overtake the acquisition step because it would then be attempting to process nonexistent data.

ANALYSIS

The data processing algorithm depicted in FIGS. 5B and 5C is an example of a general scheme to detect and identify dye-labeled species. It is not meant to be all-inclusive. Rather, it illustrates the primary features that are necessary in developing any real analyzer program and is exemplary of applicant' preferred embodiment.

After initializing the processing index k (as distinct from the acquisition index i), the program enters a simple loop which reads data D1(k) and D2(k) from the data arrays provided by the acquisition process. The program then asks whether the current point is on a peak. A number of algorithms exist which can determine this condition; details are not needed here. The term "peak" is meant in a general sense. A peak in D1 will generally be accompanied by a peak in D2. However, depending on the identity of the dye, the peaks in these two channels may differ considerably in intensity. They will, however, coincide in time. Therefore, a weighted average of the two signals, the stronger of the two signals, or some other combination of D1(k) and D2(k) could be used to define a "peak" in time.

If the current processed point is not on a peak, the index k is incremented and compared with the acquisition index i. If k equals $I_{(total)}$, the run is over and the program stops. If k is less than i, the next data points are fetched from the arrays D1 and D2 and the loop executes again. If k is equal to i, it means that processing has caught up with the data acquisition. In this event, the processing program waits a small period of time (typically a second) and again tests the values of k and i until processing can resume.

If the current processed point is on a peak, the index m is incremented. Index m counts the number of points across the current peak. The values D1(k) and D2(k) are placed in temporary array called D1peak(m) and D2peak(m), respectively. The program then tests whether the current point is the last point of the peak. If this is not the last point on the peak, program control returns to the upper loop which increments k, tests its value against i, and reads the next pair of data from the arrays D1 and D2.

Figure 6:
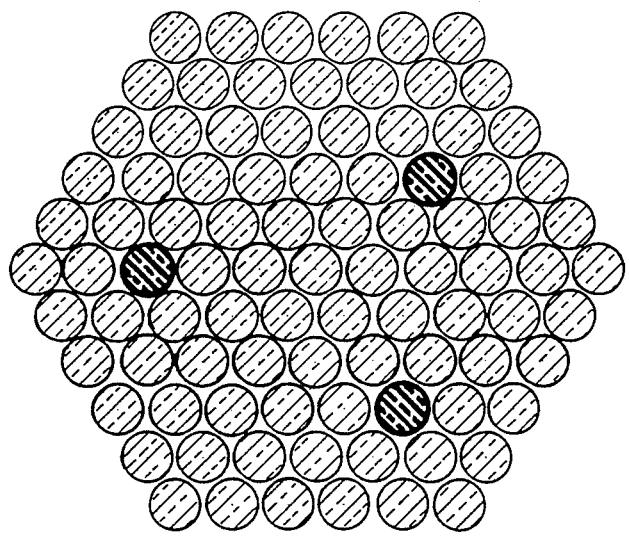
FIG. 6 is a pictorial view of a transmission filter utilizing optical fibers.

If the current pair is the last point on the peak, the peak counter is incremented and the program proceeds to determine the identity of the peak. The result is the identity of the next base in the DNA sequence. The program calculates the function W for the current peak as described above, using the arrays D1peak(m) and D2peak(m) as input data. Each nucleotide base will have associated with it a pair of peaks which give a characterstic W. Thus, based on the value of W for this peak, the program gives as output the DNA base identity A, T, C, G. The peak point index m and the arrays D1peak and D2peak are reset to 0, and the program again enters the upper data acquisition loop as shown in FIG. 6B.

The above scheme may be extended to a multi-sample scanner. In a multiple-channel instrument, the laser beam would be moved to the next sample position before re-entering the data acquisition loop in FIG. 5A. In addition, separate data arrays (for example D1A(i), D1B(i) . . . D1K(i) and D2A(i), D2B(i) . . . D2K(i) for lanes A, B, . . . K) would be assigned to each lane or sample position. Data acquisition and processing would proceed for each lane in turn in a manner similar to that described above.

We claim:

1. In a system for detecting the presence of radiant energy emitted from different species, following separation in time and/or space, and the identity of such species, having first detection means responsive to the radiant energy emitted by the species for generating a first signal that varies in amplitude in a first sense as a function of the nature of the species, second detection means responsive to the radiant energy for generating a second signal that varies in amplitude in a second sense different than the first sense as a function of the nature of the species, and third means responsive to the first and second signals for obtaining a third signal corresponding to the ratio of functions of the first and second signals, the amplitude of the third signal being indicative of the identity of each of the species, the improvement wherein the first and second detection means each include:

a detector having a large solid entrance angle positioned adjacent the species to receive radiant energy emitted from the species for generating one of the first and second signals, a wavelength selective filter means positioned between each respective detector and the species, each wavelength filter means having transmission vs. wavelength characteristics that are complementary, and wherein at least one of the first and second detection means includes a transmission filter means for rejecting radiant energy incident on the transmission filter means at an angle greater than a predetermined value.

2. A system as set forth in claim 1 which also includes a laser adapted to direct an exciting beam of radiant energy to the species, the laser beam of radiant energy having a wavelength lying within the excitation region of the species.

3. A system as set forth in claim 2 wherein the transmission filter means is associated with the wavelength filter means having a passband closest to the wavelength of the laser beam radiant energy.

4. A system as set forth in claim 3 which includes means adapted to separate fragments of DNA or other molecules labeled with emitting species of materials, positioned to be excited by radiant energy from the laser.

5. A system as set forth in claim 4 wherein the first and second detection means are positioned on opposite sides of the region propagating the laser beam of radiant energy.

6. A system as set forth in claim 2 which includes means adapted to separate fragments of DNA or other molecules labeled with emitting species of materials, positioned to be excited by radiant energy.

7. A system as set forth in claim 2 wherein the first and second detection means are positioned on opposite sides of the region propagating the laser beam of radiant energy.

8. A system as set forth in claim 7 which includes means adapted to separate fragments of DNA or other molecules labeled with emitting species of materials and means to sweep the laser beam of radiant energy across the separation means to excite the species in sequence.

9. A system as set forth in claim 8 wherein the wavelength selective filter means has transition in their transmission vs. wavelength characteristics centered at about the middle of the species' radiant energy spectra.

10. A system as set forth in claim 9 wherein the transmission filter means has an extra mural absorber among plural optical fibers positioned to have parallel generatrices transverse to the first and second detectors.

11. A system as set forth in claim 10 characterized by the absence of a lens between the first and second detection means and the emitting species.

12. A system as set forth in claim 10 wherein the predetermined value of the rejecting angle of the transmission filter means is about 22°.

13. A system as set forth in claim 1 which includes a laser and means adapted to separate fragments of DNA or other molecules labeled with emitting species of materials, positioned to be excited by radiant energy from the laser.

14. A system as set forth in claim 1 which includes a region of exciting radiation for the species and wherein the first and second detection means are positioned on opposite sides of the region containing exciting radiation.

15. A system as set forth in claim 14 wherein the wavelength selective filter means has a transition in its transmission vs. wavelength characteristics centered at about the middle of the species' radiant energy spectra.

16. A system as set forth in claim 1 wherein each detection means has a transmission filter means.

17. A system as set forth in claim 16 wherein the wavelength selective filters means each have a transition in their transmission vs. wavelength characteristic centered at about the middle of the species' emission spectra.

18. A system as set forth in claim 19 wherein each transmission filter means has an extra mural absorber among plural optical fibers positioned to have parallel generatrices transverse to the first and second detection means.

19. A system as set forth in claim 1 wherein the transmission filter means has an extra mural absorber among plural optical fibers positioned to have parallel generatrices transverse to the first and second detection means.

20. Apparatus for detecting the presence of fluorescent radiation derived from fragments of DNA or other molecules labelled according to type with different fluorescing species of materials comprising:

separation means adapted to spacially separate the molecules, means including a laser to sweep in a first plane a beam of radiant energy across the separation means to excite the species, first and second photodetectors having large solid entrance angle positioned on opposite sides of the first plane to convert fluorescent radiation emitted from the species into first and second signals, first and second wavelength filters having complementary transmission-wavelength characteristics interposed between the respective photodetectors and the separation means, a transmission filter, interposed between one of the respective photodetectors and its separation means, for rejecting radiation incidence on the photodetector at an angle greater than a predetermined value, and means responsive to the first and second signal for deriving a third signal corresponding to the ratio of functions of the first and second signals, the third signal being indicative of the identity of the fluorescing species.

21. Apparatus as set forth in claim 20 wherein the wavelength filters have transitions in their transmission vs. wavelength characteristics centered at about the middle of the wavelengths of fluorescent radiation emitted by the species.

22. Apparatus as set forth in claim 21 wherein the transmission filter has an extra mural absorber among plural optical fibers positioned to have parallel generatrices transverse to the first and second detector means.

23. Apparatus as set forth in claim 22 characterized by the absence of a lens between the first and second detector means and the emitting species.

24. Apparatus as set forth in claim 23 wherein the predetermined value of the rejection angle of the transmission filter is about 22°.

25. Apparatus as set forth in claim 20 wherein the transmission filter has an extra mural absorber among plural optical fibers positioned to have parallel generatrices transverse to the first and second detector means.

26. Apparatus as set forth in claim 20 characterized by the absence of a lens between the first and second detector means and the emitting species.

* * * * *